US012484610B2

(12) United States Patent
Sebastian et al.

(10) Patent No.: US 12,484,610 B2
(45) Date of Patent: Dec. 2, 2025

(54) AEROSOL DELIVERY DEVICE INCLUDING A SEGREGATED SUBSTRATE

(71) Applicant: R.J. REYNOLDS TOBACCO COMPANY, Winston-Salem, NC (US)

(72) Inventors: Andries Sebastian, Winston-Salem, NC (US); Serban Moldoveanu, Winston-Salem, NC (US); Balager Ademe, Winston-Salem, NC (US); Cynthia Stokes, Lexington, NC (US); Stephen B. Sears, Siler City, NC (US); S. Keith Cole, Advance, NC (US); Gary M. Dull, Lewisville, NC (US); Jannell Rowe, Clemmons, NC (US); Billy T. Conner, Clemmons, NC (US)

(73) Assignee: R.J. REYNOLDS TOBACCO COMPANY, Winston-Salem, NC (US)

( * ) Notice: Subject to any disclaimer, the term of this patent is extended or adjusted under 35 U.S.C. 154(b) by 692 days.

(21) Appl. No.: 16/850,802

(22) Filed: Apr. 16, 2020

(65) Prior Publication Data

US 2021/0321655 A1 Oct. 21, 2021

(51) Int. Cl.
*A24F 40/20* (2020.01)
*A24B 15/167* (2020.01)
(Continued)

(52) U.S. Cl.
CPC ............ *A24B 15/167* (2016.11); *A24D 1/045* (2013.01); *A24D 1/20* (2020.01); *A24D 1/22* (2020.01);
(Continued)

(58) Field of Classification Search
CPC .. A24D 1/22; A24D 1/20; A24D 1/045; A24F 42/10; A24F 42/00; A24F 42/60;
(Continued)

(56) References Cited

U.S. PATENT DOCUMENTS 1,541,891 A 6/1925 Becker
1,607,132 A 11/1926 Shichigoro
(Continued)

FOREIGN PATENT DOCUMENTS

CN 1541577 11/2004
CN 2719043 8/2005
(Continued)

OTHER PUBLICATIONS

Stephenson, "A 'Safer' Cigarette? Prove It, Say Critics", JAMA, 2000, 283(19), pp. 2507-2508. doi:10.1001/jama.283.19.2507.
(Continued)

*Primary Examiner* — Philip Y Louie
*Assistant Examiner* — Yana B Krinker
(74) *Attorney, Agent, or Firm* — Womble Bond Dickinson (US) LLP

(57) ABSTRACT

The present disclosure provides an aerosol source member and an aerosol delivery device that includes an aerosol source member. The aerosol source member includes a segmented substrate portion that includes a first substrate segment and a second substrate segment. The first substrate segment includes a first aerosol former, the second substrate segment includes a second aerosol former different from the first aerosol former, and the second substrate segment is positioned between the first substrate segment and a downstream end of the aerosol source member. The first substrate segment and the second substrate segment are configured such that when heated by a heat source, the first substrate segment is heated to a first temperature and the second substrate segment is heated to a second temperature that is less than the first temperature.

16 Claims, 4 Drawing Sheets

(51) Int. Cl.

| | |
|---|---|
| ***A24D 1/04*** | (2006.01) |
| ***A24D 1/20*** | (2020.01) |
| ***A24D 1/22*** | (2020.01) |
| ***A24F 42/10*** | (2020.01) |
| ***A24F 42/60*** | (2020.01) |
| ***A61M 15/06*** | (2006.01) |

(52) U.S. Cl.
CPC .............. *A24F 40/20* (2020.01); *A24F 42/10* (2020.01); *A24F 42/60* (2020.01); *A61M 15/06* (2013.01); *A61M 2205/3653* (2013.01); *A61M 2205/50* (2013.01); *A61M 2205/8206* (2013.01); *A61M 2205/8262* (2013.01)

(58) Field of Classification Search
CPC .......... A24F 40/20; A24F 40/00; A24F 40/30; A24F 40/40; A24F 40/42; A24F 40/57; A24C 5/01
See application file for complete search history.

(56) References Cited

U.S. PATENT DOCUMENTS 1,941,531 A 1/1934 Blankenship
2,008,433 A 7/1935 Ashour
2,057,353 A 10/1936 Whittemore, Jr.
2,104,266 A 1/1938 McCormick
2,779,340 A 1/1957 Lee
3,200,819 A 8/1965 Gilbert
4,708,151 A 11/1987 Shelar
4,714,082 A 12/1987 Banerjee et al.
4,922,901 A 5/1990 Brooks et al.
4,966,171 A 10/1990 Serrano et al.
4,991,606 A 2/1991 Serrano et al.
5,040,552 A 8/1991 Schleich et al.
5,060,671 A 10/1991 Counts et al.
5,060,676 A 10/1991 Hearn et al.
5,076,296 A 12/1991 Nystrom et al.
5,093,894 A 3/1992 Deevi et al.
5,159,940 A 11/1992 Hayward et al.
5,178,165 A 1/1993 DeFelice
5,240,012 A 8/1993 Ehrman et al.
5,261,424 A 11/1993 Sprinkel, Jr.
5,388,574 A 2/1995 Ingebrethsen et al.
5,530,225 A 6/1996 Hajaligol
5,592,955 A 1/1997 Keritsis
5,595,577 A 1/1997 Bensalem et al.
5,687,746 A 11/1997 Rose et al.
5,692,525 A 12/1997 Counts et al.
5,726,421 A 3/1998 Fleischhauer et al.
5,845,649 A 12/1998 Saito et al.
5,865,185 A 2/1999 Collins et al.
5,894,841 A 4/1999 Voges
6,006,757 A 12/1999 Lichtenberg
6,053,176 A 4/2000 Adams et al.
6,125,853 A 10/2000 Susa et al.
6,155,268 A 12/2000 Takeuchi
6,164,287 A 12/2000 White
6,311,694 B1 11/2001 Nichols et al.
6,345,625 B1 2/2002 Chew
6,371,127 B1 4/2002 Snaidr et al.
6,532,965 B1 3/2003 Abhulimen et al.
6,615,843 B2 9/2003 Pera
6,748,955 B2 6/2004 Snaidr et al.
7,080,649 B2 7/2006 Hcu
7,117,867 B2 10/2006 Cox et al.
7,503,330 B2 3/2009 Borschke et al.
7,600,517 B1 10/2009 Holzrichter
7,624,739 B2 12/2009 Snaidr et al.
7,832,410 B2 11/2010 Hon
8,061,361 B2 11/2011 Maeder et al.
8,151,803 B2 4/2012 Inagaki
8,302,611 B2 11/2012 Rowley
8,314,591 B2 11/2012 Terry et al.
8,365,742 B2 2/2013 Hon
8,499,766 B1 8/2013 Newton
8,528,567 B2 9/2013 Hajaligol
8,616,217 B2 12/2013 Tsurizumi et al.
8,776,803 B2 7/2014 Tarora et al.
8,863,754 B2 10/2014 Renaud et al.
8,915,255 B2 12/2014 Poget et al.
9,078,473 B2 7/2015 Worm et al.
9,149,072 B2 10/2015 Conner et al.
9,220,301 B2 12/2015 Banerjee et al.
9,301,546 B2 4/2016 Thomas et al.
9,332,784 B2 5/2016 Banerjee et al.
9,439,453 B2 9/2016 Conner et al.
9,532,591 B2 1/2017 Mironov
9,549,572 B2 1/2017 Dincer et al.
9,609,893 B2 4/2017 Novak, III et al.
9,629,393 B2 4/2017 Stolz et al.
9,717,273 B2 8/2017 Poget et al.
9,730,468 B2 8/2017 Poget et al.
9,801,412 B2 10/2017 Grant
9,894,930 B2 2/2018 Bonici et al.
9,918,494 B2 3/2018 Mironov et al.
9,930,915 B2 4/2018 Worm et al.
9,943,114 B2 4/2018 Batista
10,034,493 B2 7/2018 Akiyama et al.
10,111,463 B2 10/2018 Batista
10,159,277 B2 12/2018 Bonnely
10,212,968 B2 2/2019 Mironov et al.
2005/0016550 A1 1/2005 Katase
2006/0196518 A1 9/2006 Hon
2007/0215168 A1* 9/2007 Banerjee .................. A24D 1/22 131/335
2008/0092912 A1 4/2008 Robinson et al.
2009/0065011 A1 3/2009 Maeder et al.
2009/0095311 A1 4/2009 Hon
2009/0126745 A1 5/2009 Hon
2009/0188490 A1 7/2009 Hon
2009/0272379 A1 11/2009 Thorens et al.
2011/0083674 A1 4/2011 Karpinsky
2011/0094523 A1 4/2011 Thorens et al.
2011/0126848 A1 6/2011 Zuber et al.
2011/0155718 A1 6/2011 Greim et al.
2011/0168194 A1 7/2011 Hon
2011/0265806 A1 11/2011 Alarcon et al.
2011/0290248 A1 12/2011 Schennum
2012/0111347 A1 5/2012 Hon
2012/0260927 A1 10/2012 Liu
2012/0279512 A1 11/2012 Hon
2013/0037041 A1 2/2013 Worm et al.
2013/0056013 A1 3/2013 Terry et al.
2013/0133675 A1* 5/2013 Shinozaki ................ A24D 1/22 131/329
2013/0167850 A1 7/2013 Al-Aawar
2013/0228190 A1 9/2013 Weiss et al.
2013/0306084 A1 11/2013 Flick
2014/0000638 A1 1/2014 Sebastian et al.
2014/0048085 A1 2/2014 Cox
2014/0060554 A1 3/2014 Collett et al.
2014/0060555 A1 3/2014 Chang et al.
2014/0096781 A1 4/2014 Sears et al.
2014/0096782 A1 4/2014 Ampolini et al.
2014/0209105 A1 7/2014 Sears et al.
2014/0253144 A1 9/2014 Novak et al.
2014/0261408 A1 9/2014 DePiano et al.
2014/0261486 A1 9/2014 Potter et al.
2014/0261487 A1 9/2014 Chapman et al.
2014/0261495 A1 9/2014 Novak et al.
2014/0270727 A1 9/2014 Ampolini et al.
2014/0270729 A1 9/2014 DePiano et al.
2014/0270730 A1 9/2014 DePiano et al.
2015/0034100 A1 2/2015 Park et al.
2015/0040924 A1 2/2015 Mironov et al.
2015/0296882 A1 10/2015 Mironov et al.
2015/0342254 A1 12/2015 Mironov et al.
2016/0007648 A1 1/2016 Sutton et al.
2016/0007649 A1 1/2016 Sampson et al.
2016/0022930 A1* 1/2016 Greim ..................... A24F 40/30 131/328
2016/0120216 A1 5/2016 Mironov et al.
2016/0135495 A1 5/2016 Poget et al.

(56) References Cited

U.S. PATENT DOCUMENTS

| | | | |
|---|---|---|---|
| 2016/0174609 | A1 | 6/2016 | Mironov |
| 2016/0192704 | A1 | 7/2016 | Bonnely |
| 2016/0316816 | A1 | 11/2016 | Lavanchy et al. |
| 2016/0360785 | A1 | 12/2016 | Bless et al. |
| 2017/0000189 | A1 | 1/2017 | Mironov et al. |
| 2017/0055577 | A1 | 3/2017 | Batista |
| 2017/0055578 | A1 | 3/2017 | Oda et al. |
| 2017/0164654 | A1 | 6/2017 | Ademe |
| 2017/0196261 | A1 | 7/2017 | Borges De Couraca et al. |
| 2017/0238607 | A1* | 8/2017 | Nordskog ................ A24D 1/02 |
| 2017/0303585 | A1 | 10/2017 | Florack et al. |
| 2017/0318859 | A1 | 11/2017 | Batista |
| 2018/0000165 | A1 | 1/2018 | Liu |
| 2018/0014571 | A1 | 1/2018 | Nakano |
| 2018/0070640 | A1 | 3/2018 | Bessant et al. |
| 2018/0116280 | A1 | 5/2018 | Maiwald et al. |
| 2018/0192707 | A1 | 7/2018 | Worm et al. |
| 2018/0317560 | A1 | 11/2018 | Shinozaki et al. |
| 2018/0325167 | A1 | 11/2018 | Grant |
| 2018/0368468 | A1 | 12/2018 | Mishra et al. |
| 2019/0000135 | A1 | 1/2019 | Lavanant et al. |
| 2019/0000141 | A1 | 1/2019 | Rojo-Calderon et al. |
| 2019/0000142 | A1 | 1/2019 | Lavanchy et al. |
| 2019/0014818 | A1 | 1/2019 | Saygili |
| 2019/0014820 | A1 | 1/2019 | Malgat |
| 2019/0014821 | A1 | 1/2019 | Batista et al. |
| 2019/0059449 | A1 | 2/2019 | Akiyama et al. |
| 2019/0059450 | A1 | 2/2019 | Akiyama et al. |
| 2019/0075848 | A1 | 3/2019 | Worm et al. |
| 2019/0082735 | A1 | 3/2019 | Phillips et al. |
| 2019/0281891 | A1* | 9/2019 | Hejazi .................... A24B 13/02 |

FOREIGN PATENT DOCUMENTS

| | | | |
|---|---|---|---|
| CN | 201379072 | 1/2010 | |
| EP | 0 295 122 | 12/1988 | |
| EP | 0 845 220 | 6/1998 | |
| EP | 1 618 803 | 1/2006 | |
| GB | 2469850 | 11/2010 | |
| WO | WO1995034226 | 12/1995 | |
| WO | WO1998054989 | 12/1998 | |
| WO | WO 2003/034847 | 5/2003 | |
| WO | WO 2004/080216 | 9/2004 | |
| WO | WO 2005/099494 | 10/2005 | |
| WO | WO 2007/131449 | 11/2007 | |
| WO | WO2009022232 | 2/2009 | |
| WO | WO2013072336 | 5/2013 | |
| WO | WO2013149810 | 10/2013 | |
| WO | WO2013189836 | 12/2013 | |
| WO | WO2014037270 | 3/2014 | |
| WO | WO2014156838 | 10/2014 | |
| WO | 2015/000974 A1 | 1/2015 | |
| WO | WO2015097005 | 7/2015 | |
| WO | WO2015128384 | 9/2015 | |
| WO | WO2015151158 | 10/2015 | |
| WO | WO2015184744 | 12/2015 | |
| WO | WO2015197850 | 12/2015 | |
| WO | WO2017042297 | 3/2017 | |
| WO | WO2017108912 | 6/2017 | |
| WO | WO2017114760 | 7/2017 | |
| WO | WO2017115181 | 7/2017 | |
| WO | WO2017115182 | 7/2017 | |
| WO | WO2017115183 | 7/2017 | |
| WO | WO2017115184 | 7/2017 | |
| WO | WO2017115185 | 7/2017 | |
| WO | WO2017115188 | 7/2017 | |
| WO | WO2017115196 | 7/2017 | |
| WO | WO2017207442 | 12/2017 | |
| WO | WO2017212284 | 12/2017 | |
| WO | WO2018170800 | 9/2018 | |
| WO | WO2018201655 | 11/2018 | |
| WO | WO2019010680 | 1/2019 | |
| WO | WO-2020025730 A1 * | 2/2020 | ............. A24B 15/14 |

OTHER PUBLICATIONS

"Chemical and Biological Studies on New Cigarette Prototypes That Heat Instead of Burn Tobacco", R. J. Reynolds Tobacco Company, 1988.

International Search Report in the corresponding International Application No. PCT/IB2021/053086, dated Jul. 5, 2021, 7 pages.

* cited by examiner

AEROSOL DELIVERY DEVICE INCLUDING A SEGREGATED SUBSTRATE

BACKGROUND

Field of the Disclosure

The present disclosure relates to aerosol delivery devices and uses thereof for yielding aerosol precursor compositions in inhalable form. More particularly, the present disclosure relates to aerosol source members containing substrate materials for aerosol delivery devices and systems, such as smoking articles, that utilize electrically-generated heat or combustible heat sources to heat aerosol precursor compositions, preferably without significant combustion, in order to provide an inhalable substance in the form of an aerosol for human consumption.

Description of Related Art

Many smoking articles have been proposed through the years as improvements upon, or alternatives to, smoking products based upon combusting tobacco for use. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference in its entirety.

The point of some of the improvements or alternatives to smoking articles has been to provide the sensations associated with cigarette, cigar, or pipe smoking without delivering considerable quantities of incomplete combustion and pyrolysis products. To this end numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Patent Application Publication Nos. 2013/0255702 to Griffith, Jr. et al.; and 2014/0096781 to Sears et al., which are incorporated herein by reference in their entireties.

Articles that produce the taste and sensation of smoking by electrically heating tobacco, tobacco-derived materials, or other plant derived materials have suffered from inconsistent performance characteristics. For example, some articles have suffered from inconsistent release of flavors or other inhalable materials and inadequate loading of aerosol precursor compositions on substrates. Accordingly, it can be desirable to provide a smoking article that can provide the sensations of cigarette, cigar, or pipe smoking that does so without combusting the substrate material and that does so with advantageous performance characteristics.

BRIEF SUMMARY

In various embodiments, the present disclosure provides an aerosol source member configured to generate an aerosol for delivery, and an aerosol delivery device that includes an aerosol source member. The present disclosure includes, without limitation, the following example embodiments:

An aerosol source member configured to generate an aerosol for delivery, the aerosol source member comprising a segmented substrate portion comprising a first substrate segment including a first aerosol former, and a second substrate segment including a second aerosol former different from the first aerosol former, the second substrate segment positioned between the first substrate segment and a downstream end of the aerosol source member, wherein the first substrate segment and the second substrate segment are configured such that when heated by a heat source, the first substrate segment is heated to a first temperature and the second substrate segment is heated to a second temperature that is less than the first temperature.

The aerosol source member of any preceding example embodiment, or any combination of any preceding example embodiments, wherein the first substrate segment comprises a tobacco free material and the second substrate segment comprises a tobacco material.

The aerosol source member of any preceding example embodiment, or any combination of any preceding example embodiments, wherein the first temperature is configured to aerosolize the first aerosol former without substantial degradation of the first aerosol former and the second temperature is configured to aerosolize the second aerosol former without substantial degradation of the second aerosol former.

The aerosol source member of any preceding example embodiment, or any combination of any preceding example embodiments, wherein the first temperature is capable of degrading the second aerosol former.

The aerosol source member of any preceding example embodiment, or any combination of any preceding example embodiments, wherein the first aerosol former includes at least one of maltol, vanillin, ethyl vanillin, cinnamic acid, phenylacetic acid, levulinic acid, nerolidol, citronellyl phenylacetate, caryophylene oxide, gamma-nonalactone, isoamyl phenylacetate, phenylethyl isovalerate, heliotropin, nicotine lactate, nicotine levulinate, or nicotine benzoate.

The aerosol source member of any preceding example embodiment, or any combination of any preceding example embodiments, wherein the second aerosol former includes at least one of 2-acetyl pyrrole, methyl cyclopentenolone, alpha-ionone, geraniol, beta-damascene, menthol, caryophyllene, caproic acid, phenethyl alcohol, anethole, phenethyl butyrate, alpha terpineol, ethyl phenylacetate, 3-methylvaleric acid, propylene glycol, benzyl alcohol, nicotine L-malate, or nicotine mucate.

The aerosol source member of any preceding example embodiment, or any combination of any preceding example embodiments, wherein the first aerosol former includes a nanocellulose material impregnated with an aerosol precursor composition.

The aerosol source member of any preceding example embodiment, or any combination of any preceding example embodiments, wherein the second aerosol former includes the nanocellulose material impregnated with another aerosol precursor composition.

The aerosol source member of any preceding example embodiment, or any combination of any preceding example embodiments, wherein the segmented substrate portion comprises a third substrate segment including a third aerosol former, the third substrate segment positioned between the second substrate segment and the downstream end of the aerosol source member.

The aerosol source member of any preceding example embodiment, or any combination of any preceding example embodiments, wherein the third substrate segment comprises a tobacco material.

The aerosol source member of any preceding example embodiment, or any combination of any preceding example embodiments, wherein the third aerosol former includes at least one of 3-acetylpyridine, tetramethylpyrazine, methyl salicylate, linalool, ethyl caproate, gamma-valerolactone, para-tolylaldehyde, 2-methylbutyric acid, isovaleric acid, benzaldehyde, limonene, or 2-methylpyrazine.

The aerosol source member of any preceding example embodiment, or any combination of any preceding example embodiments, further comprising a heat source located proximate the first substrate segment, wherein the heat source is integral with the aerosol source member.

The aerosol source member of any preceding example embodiment, or any combination of any preceding example embodiments, wherein the heat source is a combustible heat source.

The aerosol source member of any preceding example embodiment, or any combination of any preceding example embodiments, further comprising a filter located proximate the downstream end of the aerosol source member.

The aerosol source member of any preceding example embodiment, or any combination of any preceding example embodiments, further comprising a first barrier positioned between the heat source and the first substrate segment, the first barrier configured to prevent the first substrate segment from exceeding the first temperature.

The aerosol source member of any preceding example embodiment, or any combination of any preceding example embodiments, further comprising a second barrier positioned between the first substrate segment and the second substrate segment, the second barrier configured to prevent the second substrate segment from exceeding the second temperature.

The aerosol source member of any preceding example embodiment, or any combination of any preceding example embodiments, wherein the first temperature is in a range of approximately 200° C. to approximately 300° C. and the second temperature is in a range of approximately 100° C. to approximately 200° C.

The aerosol source member of any preceding example embodiment, or any combination of any preceding example embodiments, wherein the heat source comprises a first heating segment and a second heating segment, the first heating segment configured to heat the first substrate segment to the first temperature, and the second heating segment configured to heat the second substrate segment to the second temperature.

The aerosol source member of any preceding example embodiment, or any combination of any preceding example embodiments, wherein the first heating segment is disposed along at least a portion of the first substrate segment and the second heating segment is disposed along at least a portion of the second substrate segment.

The aerosol source member of any preceding example embodiment, or any combination of any preceding example embodiments, wherein the first heating segment is disposed about the first substrate segment and the second heating segment is disposed about the second substrate segment.

The aerosol source member of any preceding example embodiment, or any combination of any preceding example embodiments, wherein the first and second heating segments are electrically powered heating elements.

The aerosol source member of any preceding example embodiment, or any combination of any preceding example embodiments, wherein at least one of the first or second heating segments comprises a resistive heating element.

The aerosol source member of any preceding example embodiment, or any combination of any preceding example embodiments, wherein at least one of the first or second heating segments comprises an inductive heating element.

The aerosol source member of any preceding example embodiment, or any combination of any preceding example embodiments, wherein the substrate portion defines an aerosol pathway extending towards the downstream end of the aerosol source member.

An aerosol delivery device comprising a control body configured to receive at least a portion of an aerosol source member, and a heat source, wherein the aerosol source member comprises a segmented substrate portion comprising a first substrate segment including a first aerosol former, and a second substrate segment including a second aerosol former different from the first aerosol former, the second substrate segment positioned between the first substrate segment and a downstream end of the aerosol source member, and wherein the heat source is configured to heat the first substrate segment to a first temperature and the second substrate segment to a second temperature that is less than the first temperature.

The aerosol delivery device of any preceding example embodiment, or any combination of any preceding example embodiments, wherein the control body includes the heat source, and wherein the heat source comprises a first heating segment and a second heating segment, the first heating segment configured to heat the first substrate segment to the first temperature, and the second heating segment configured to heat the second substrate segment to the second temperature.

The aerosol delivery device of any preceding example embodiment, or any combination of any preceding example embodiments, wherein the control body includes a power source configured to provide energy to the first and second heating segments.

The aerosol delivery device of any preceding example embodiment, or any combination of any preceding example embodiments, wherein the control body includes a controller configured to control energy transmitted to the first and second heating segments.

The aerosol delivery device of any preceding example embodiment, or any combination of any preceding example embodiments, wherein the first heating segment is disposed along the first substrate segment and the second heating segment is disposed along the second substrate segment.

The aerosol delivery device of any preceding example embodiment, or any combination of any preceding example embodiments, wherein the first heating segment is disposed about the first substrate segment and the second heating segment is disposed about the second substrate segment.

The aerosol delivery device of any preceding example embodiment, or any combination of any preceding example embodiments, wherein the first and second heating segments are electrically powered heating elements.

The aerosol delivery device of any preceding example embodiment, or any combination of any preceding example embodiments, wherein at least one of the first or second heating segments comprises a resistive heating element.

The aerosol delivery device of any preceding example embodiment, or any combination of any preceding example embodiments, wherein at least one of the first or second heating segments comprises an inductive heating element.

The aerosol delivery device of any preceding example embodiment, or any combination of any preceding example embodiments, wherein the substrate portion defines an aerosol pathway extending towards the downstream end of the aerosol source member.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
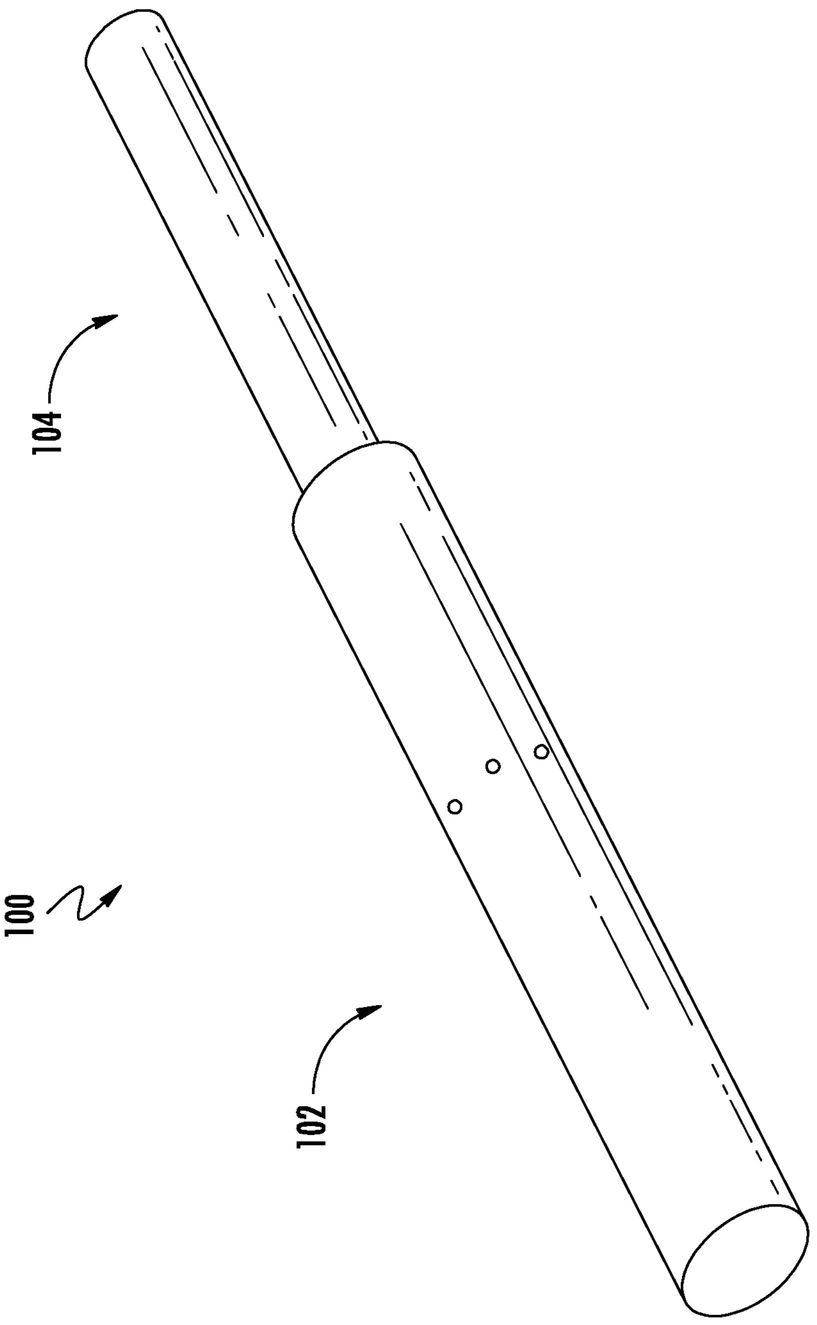
Figure 2:
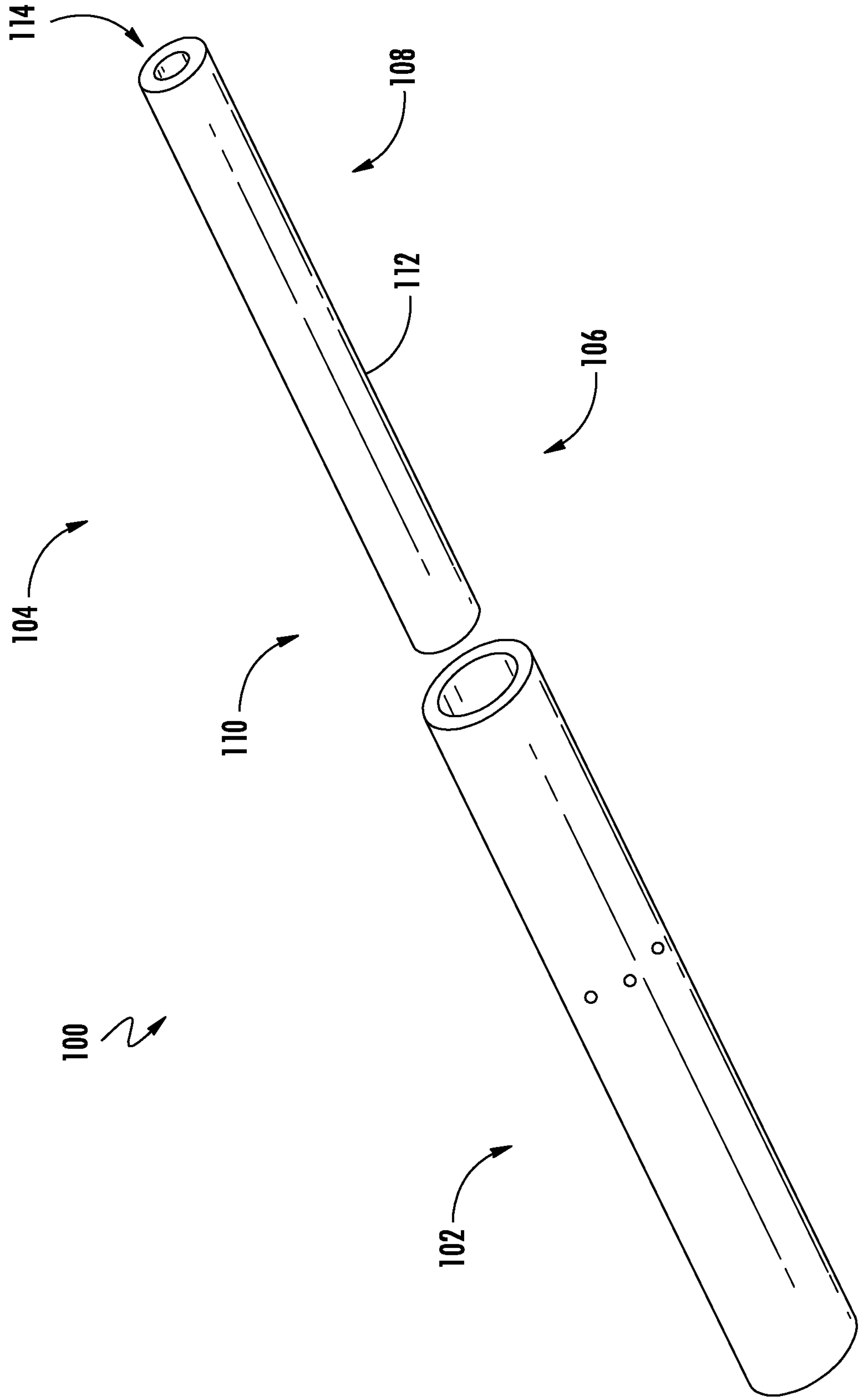
Figure 3:
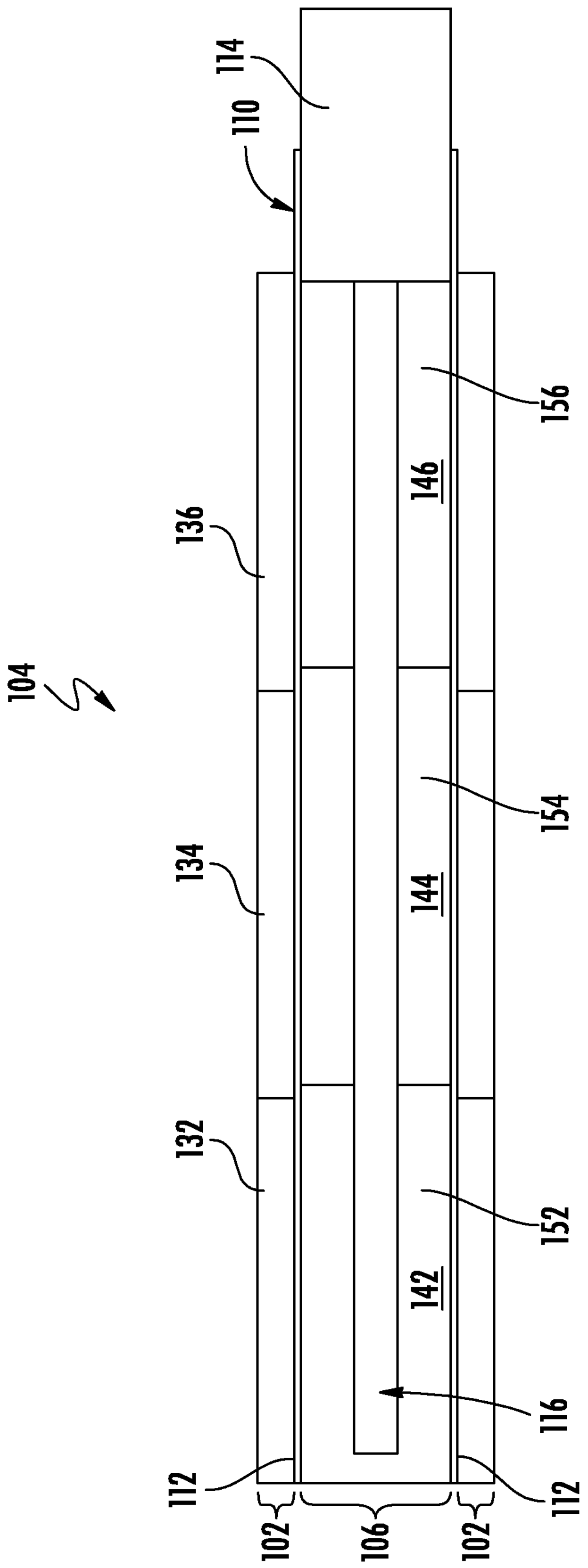
Figure 4:
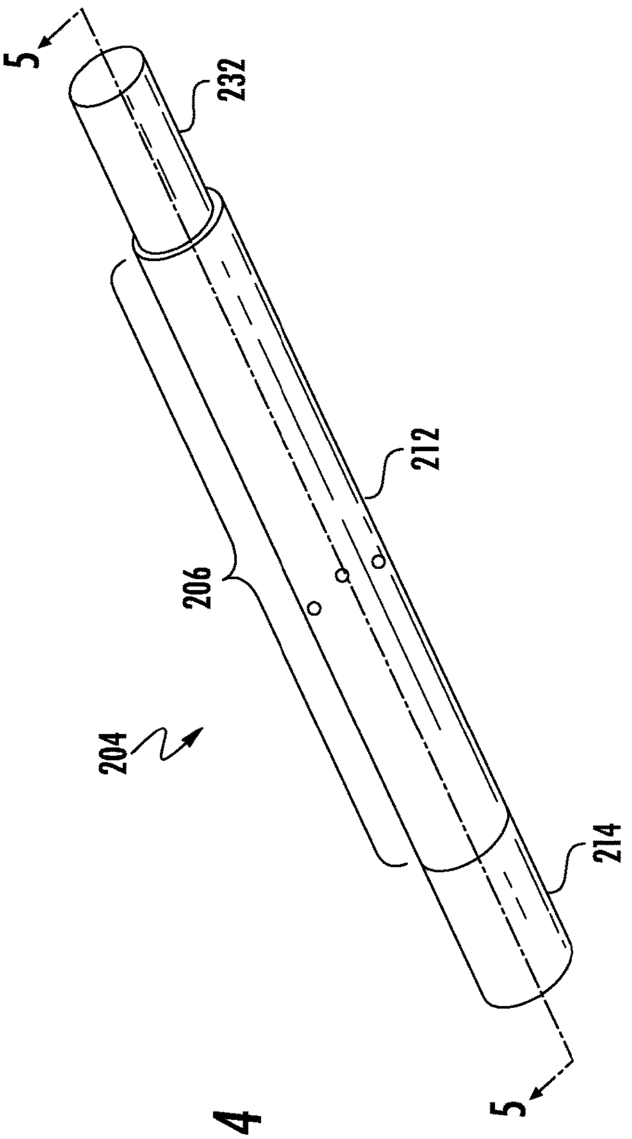
Figure 5:
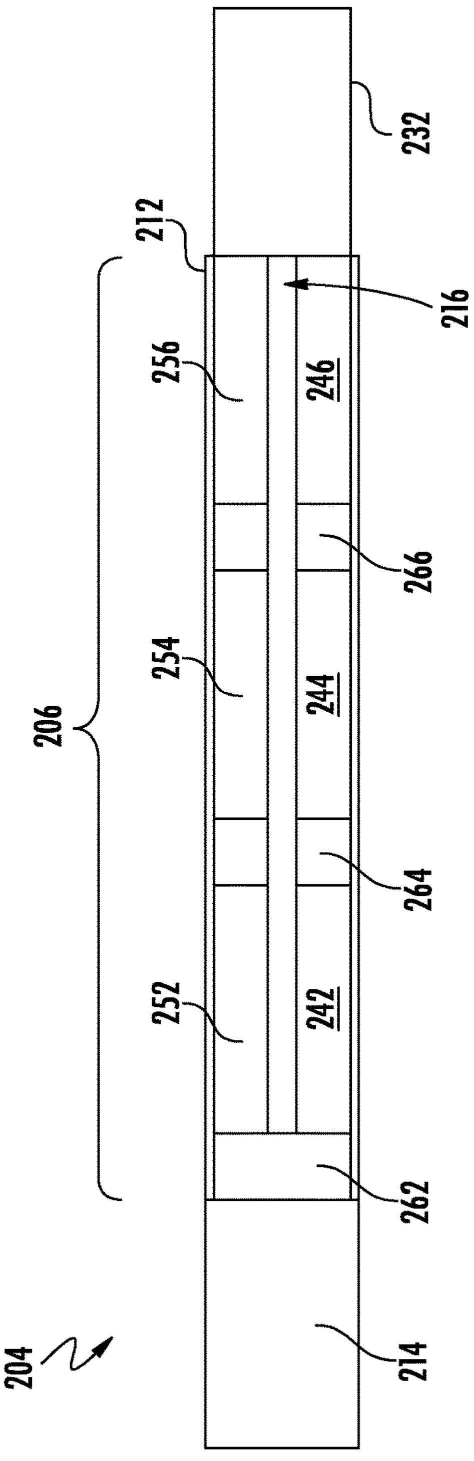

Having thus described aspects of the disclosure in the foregoing general terms, reference will now be made to the accompanying drawings, which are not necessarily drawn to scale, and wherein:

FIG. 1 illustrates a perspective view of an aerosol delivery device comprising a control body and an aerosol source member, wherein the aerosol source member and the control body are coupled to one another, according to an example embodiment of the present disclosure;

FIG. 2 illustrates a perspective view of the aerosol delivery device of FIG. 1 wherein the aerosol source member and the control body are decoupled from one another, according to an example embodiment of the present disclosure;

FIG. 3 illustrates a schematic cross-section drawing of the aerosol source member of FIG. 2, according to an example embodiment of the disclosure;

FIG. 4 illustrates a perspective view of another aerosol source member, according to an example embodiment of the present disclosure; and FIG. 5 illustrates a schematic cross-sectional view taken along section line 5-5 of FIG. 4.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like. As used herein, "substantially free" refers to concentrations of a given substance of less than 1% by weight or less than 0.5% by weight or less than 0.1% by weight based on total weight of a material.

Some embodiments of aerosol source members according to the present disclosure use electrical energy to heat a material to form an inhalable substance (e.g., electrically heated tobacco products). Other embodiments of aerosol source members according to the present disclosure use an ignitable heat source to heat a material to form an inhalable substance (e.g., carbon heated tobacco products). The material may be heated without combusting the material to any significant degree. Components of such systems have the form of articles that are sufficiently compact to be considered hand-held devices. That is, use of components of aerosol delivery devices does not result in the production of smoke in the sense that aerosol results principally from by-products of combustion or pyrolysis of tobacco, but rather, use of those systems results in the production of vapors resulting from volatilization or vaporization of certain components incorporated therein. In some example embodiments, components of aerosol delivery devices may be characterized as electronic cigarettes, and those electronic cigarettes may incorporate tobacco and/or components derived from tobacco, and hence deliver tobacco derived components in aerosol form.

In some embodiments, the heat source may be configured to generate heat upon ignition thereof. For example, in some embodiments, the heat source may comprise a combustible fuel element that incorporates a combustible carbonaceous material. In other embodiments, the heat source may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite a hollow cylindrical (e.g., tube) fibers; iron oxide powder; glass filaments; powdered calcium carbonate; alumina granules; ammonia sources, such as ammonia salts; and/or binding agents, such as guar gum, ammonium alginate and sodium alginate). In other embodiments, the heat source may comprise a plurality of ignitable objects, such as, for example, a plurality of ignitable beads. In other embodiments, the heat source may differ in composition or relative content amounts from those listed above. For example, in some embodiments different forms of carbon could be used as a heat source, such as graphite or graphene. In other embodiments, the heat source may have increased levels of activated carbon, different porosities of carbon, different amounts of carbon, blends of any above mentioned components, etc. In still other embodiments, the heat source may comprise a non-carbon heat source, such as, for example, a combustible liquefied gas configured to generate heat upon ignition thereof. For example, in some embodiments, the liquefied gas may comprise one or more of petroleum gas (LPG or LP-gas), propane, propylene, butylenes, butane, isobutene, methyl propane, or n-butane. In still other embodiments, the heat source may comprise a chemical reaction based heat source, wherein ignition of the heat source comprises the interaction of two or more individual components. For example, a chemical reaction based heat source may comprise metallic agents and an activating solution, wherein the heat source is activated when the metallic agents and the activating solution come in contact. Some examples of chemical based heat sources can be found in U.S. Pat. No. 7,290,549 to Banerjee et al., which is incorporated herein by reference in its entirety. Combinations of heat sources are also possible.

Aerosol generating components of certain aerosol delivery devices and/or aerosol source members may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol delivery device in accordance with some example embodiments of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of embodiments associated with aerosol delivery devices and/or aerosol source members such as so-called “e-cigarettes” or “tobacco heating products,” it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices and/or aerosol source members of the present disclosure may also be characterized as being vapor-producing articles or medicament delivery articles. Thus, such articles or devices may be adapted to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term “aerosol” as used herein is meant to include vapors, gases, and aerosols of a form or type suitable for human inhalation, whether or not visible, and whether or not of a form that might be considered smoke-like. The physical form of the inhalable substance is not necessarily limited by the nature of the inventive devices but rather may depend upon the nature of the medium and the inhalable substance itself as to whether it exists in a vapor state or an aerosol state. In some embodiments, the terms “vapor” and “aerosol” may be interchangeable. Thus, for simplicity, the terms “vapor” and “aerosol” as used to describe aspects of the disclosure are understood to be interchangeable unless stated otherwise.

In some embodiments, aerosol delivery devices of the present disclosure may comprise some combination of a power source (e.g., an electrical power source), at least one control component (e.g., means for actuating, controlling, regulating, and ceasing power for heat generation, such as by controlling electrical current flow from the power source to other components of the article (e.g., a microprocessor, individually or as part of a microcontroller)), a heating source (e.g., an electrical resistance heating element or other component and/or an inductive coil or other associated components and/or one or more radiant heating elements), and an aerosol source member that includes a substrate portion capable of yielding an aerosol upon application of sufficient heat. Note that it is possible to physically combine one or more of the above-noted components. For instance, in certain embodiments, a conductive heater trace can be printed on the surface of a substrate material as described herein (e.g., a nanocellulose substrate film) using a conductive ink such that the heater trace can be powered by the power source and used as the resistance heating element. Example conductive inks include graphene inks and inks containing various metals, such as inks including silver, gold, palladium, platinum, and alloys or other combinations thereof (e.g., silver-palladium or silver-platinum inks), which can be printed on a surface using processes such as gravure printing, flexographic printing, off-set printing, screen printing, ink-jet printing, or other appropriate printing methods.

In various embodiments, a number of these components may be provided within an outer body or shell, which, in some embodiments, may be referred to as a housing. The overall design of the outer body or shell may vary, and the format or configuration of the outer body that may define the overall size and shape of the aerosol delivery device may vary. Although other configurations are possible, in some embodiments, an elongated body resembling the shape of a cigarette or cigar may be a formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In embodiments, all of the components of the aerosol delivery device are contained within one housing or body. In other embodiments, an aerosol delivery device may comprise two or more housings that are joined and are separable. For example, an aerosol delivery device may possess at one end a control body comprising a housing containing one or more reusable components (e.g., an accumulator such as a rechargeable battery and/or rechargeable super capacitor and various electronics for controlling the operation of that article), and at the other end and removably coupleable thereto, an outer body or shell containing a disposable portion (e.g., a disposable flavor-containing aerosol source member).

In other embodiments, aerosol source members of the present disclosure may generally include a combustible heat source configured to heat a substrate material. The substrate material and/or at least a portion of the heat source may be covered in an outer wrap or wrapping, a casing, a component, a module, a member, or the like. The overall design of the enclosure is variable, and the format or configuration of the enclosure that defines the overall size and shape of the aerosol source member is also variable. Although other configurations are possible, the overall design, size, and/or shape of these embodiments may resemble that of a conventional cigarette or cigar. In various aspects, the heat source may be capable of generating heat to aerosolize a substrate material that comprises, for example, a substrate material associated with an aerosol precursor composition, an extruded structure and/or substrate, tobacco and/or a tobacco related material, such as a material that is found naturally in tobacco that is isolated directly from the tobacco or synthetically prepared, in a solid or liquid form (e.g., beads, sheets, shreds, a wrap), or the like.

Although an aerosol deliver device and/or an aerosol source member according to the present disclosure may take on a variety of embodiments, as discussed in detail below, the use of the aerosol delivery device and/or aerosol source member by a consumer will be similar in scope. The foregoing description of use of the aerosol delivery device and/or aerosol source member is applicable to the various embodiments described through minor modifications, which are apparent to the person of skill in the art in light of the further disclosure provided herein. The description of use, however, is not intended to limit the use of the articles of the present disclosure but is provided to comply with all necessary requirements of disclosure herein.

More specific formats, configurations, and arrangements of various substrate materials, aerosol source members, and components within aerosol delivery devices of the present disclosure will be evident in light of the further disclosure provided hereinafter. Additionally, the selection of various aerosol delivery device components may be appreciated upon consideration of the commercially available electronic aerosol delivery devices. Further, the arrangement of the components within the aerosol delivery device may also be appreciated upon consideration of the commercially available electronic aerosol delivery devices.

In this regard, FIG. 1 illustrates an aerosol delivery device 100 according to an example embodiment of the present disclosure. In the depicted embodiment, the aerosol delivery device 100 includes a control body 102 and an aerosol source member 104. In various embodiments, the aerosol source member 104 and the control body 102 may be permanently or detachably aligned in a functioning relationship. In this regard, FIG. 1 illustrates the aerosol delivery device 100 in a coupled configuration, whereas FIG. 2 illustrates the aerosol delivery device 100 in a decoupled configuration. Various mechanisms may connect the aerosol source member 104 to the control body 102 to result in a threaded engagement, a press-fit engagement, an interference fit, a sliding fit, a magnetic engagement, or the like.

In various embodiments, the aerosol delivery device 100 according to the present disclosure may have a variety of overall shapes, including, but not limited to an overall shape that may be defined as being substantially rod-like or substantially tubular shaped or substantially cylindrically shaped. The device 100 may have a substantially round cross-section; however, other cross-sectional shapes (e.g., oval, square, triangle, etc.) also are encompassed by the present disclosure. For example, in some embodiments one or both of the control body 102 or the aerosol source member 104 (and/or any subcomponents) may have a substantially rectangular shape, such as a substantially rectangular cuboid shape. In other embodiments, one or both of the control body 102 or the aerosol source member 104 (and/or any subcomponents) may have other hand-held shapes. For example, in some embodiments, the control body 102 may have a small box shape, various pod mod shapes, or a fob-shape. Thus, such language that is descriptive of the physical shape of the article may also be applied to the individual components thereof, including the control body 102 and the aerosol source member 104.

Alignment of the components within the aerosol delivery device of the present disclosure may vary across various embodiments. In some embodiments, the substrate portion may be positioned proximate a heating source to facilitate aerosol delivery to the user. Other configurations, however, are not excluded. Generally, the heating source may be positioned sufficiently near the substrate portion so that heat from the heating source can volatilize the substrate portion (as well as, in some embodiments, one or more flavorants, medicaments, or the like that may likewise be provided for delivery to a user) and form an aerosol for delivery to the user. When the heating source heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor, aerosol, or mixture thereof, wherein such terms are also interchangeably used herein except where otherwise specified.

As noted above, the aerosol delivery device 100 of various embodiments may incorporate a battery and/or other electrical power source to provide current flow sufficient to provide various functionalities to the aerosol delivery device, such as powering of the heating source, powering of control systems, powering of indicators, and the like. As will be discussed in more detail below, the power source may take on various embodiments. The power source may be able to deliver sufficient power to rapidly activate the heating source to provide for aerosol formation and power the aerosol delivery device through use for a desired duration of time. In some embodiments, the power source is sized to fit conveniently within the aerosol delivery device so that the aerosol delivery device can be easily handled. Examples of useful power sources include lithium-ion batteries that may be rechargeable (e.g., a rechargeable lithium-manganese dioxide battery). In particular, lithium polymer batteries can be used as such batteries can provide increased safety. Other types of batteries (e.g., N50-AAA CADNICA nickel-cadmium cells) may also be used. Additionally, a power source may be sufficiently lightweight to not detract from a desirable smoking experience. Some examples of possible power sources are described in U.S. Pat. No. 9,484,155 to Peckerar et al., and U.S. Patent Application Publication No. 2017/0112191 to Sur et al., filed Oct. 21, 2015, the disclosures of which are incorporated herein by reference in their respective entireties.

In specific embodiments, one or both of the control body 102 and the aerosol source member 104 may be referred to as being disposable or as being reusable. For example, the control body 102 may have a replaceable battery or a rechargeable battery, solid-state battery, thin-film solid-state battery, rechargeable super capacitor or the like, and thus may be combined with any type of recharging technology, including connection to a wall charger, connection to a car charger (e.g., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Patent Application Publication No. 2017/0112196 to Sur et al., which is incorporated herein by reference in its entirety. Further, in some embodiments, the control body 102 and/or the aerosol source member 104 may comprise a single-use device. A single use component for use with a control body is disclosed in U.S. Pat. No. 8,910,639 to Chang et al., which is incorporated herein by reference in its entirety.

In further embodiments, the power source may also comprise a capacitor. Capacitors are capable of discharging more quickly than batteries and can be charged between puffs, allowing the battery to discharge into the capacitor at a lower rate than if it were used to power the heating source directly. For example, a super capacitor (e.g., an electric double-layer capacitor (EDLC)) may be used separate from or in combination with a battery. When used alone, the super capacitor may be recharged before each use of the article. Thus, the device may also include a charger component that can be attached to the smoking article between uses to replenish the super capacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety.

In another example, an aerosol delivery device may comprise a first conductive surface configured to contact a first body part of a user holding the device, and a second conductive surface, conductively isolated from the first conductive surface, configured to contact a second body part of the user. As such, when the aerosol delivery device detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Patent Application Publication No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Patent Application Publication Nos. 2006/0196518 and 2009/0188490 to Hon; U.S. Patent Application Publication No. 2010/0024834 to Oglesby et al.; U.S. Patent Application Publication No. 2010/0307518 to Wang; PCT Patent Application Publication No. WO 2010/091593 to Hon; and PCT Patent Application Publication No. WO 2013/089551 to Foo, each of which is incorporated herein by reference in its entirety. Further, U.S. Patent Application Publication No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various embodiments, and all of the foregoing disclosures are incorporated herein by reference in their entireties.

Referring to FIG. 2, in the depicted embodiment, the aerosol source member 104 comprises a heated section 106, which is configured to be inserted into the control body 102, and a mouth section 108, upon which a user draws to create the aerosol. At least a portion of the heated section 106 may include a substrate portion 110. As will be discussed in more detail below, in various embodiments the substrate portion 110 may comprise a cellulose material (such as, for example a nanocellulose material), impregnated with an aerosol precursor composition (e.g., an aerosol former). In various embodiments, the aerosol source member 104, or a portion thereof, may be wrapped in an exterior overwrap material 112. In various embodiments, the mouth section 108 of the aerosol source member 104 may include a filter 114, which may, for example, be made of a cellulose acetate or polypropylene material. The filter 114 may additionally or alternatively contain strands of tobacco containing material, such as described in U.S. Pat. No. 5,025,814 to Raker et al., which is incorporated herein by reference in its entirety. In various embodiments, the filter 114 may increase the structural integrity of the mouth section 108 of the aerosol source member 104, and/or provide filtering capacity, if desired, and/or provide resistance to draw. In some embodiments, the filter 114 may comprise discrete segments. For example, some embodiments may include a segment providing filtering, a segment providing draw resistance, a hollow segment providing a space for the aerosol to cool, a segment providing increased structural integrity, other filter segments, and any one or any combination of the above.

In some embodiments, the material of the exterior overwrap 112 may comprise a material that resists transfer of heat, which may include a paper or other fibrous material, such as a cellulose material. The exterior overwrap material may also include at least one filler material imbedded or dispersed within the fibrous material. In various embodiments, the filler material may have the form of water insoluble particles. Additionally, the filler material may incorporate inorganic components. In various embodiments, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the exterior overwrap at the mouth section 108 of the aerosol source member may function to simply separate the substrate portion 110 from the mouth of a consumer or to provide space for positioning of a filter material, as described below, or to affect draw on the article or to affect flow characteristics of the vapor or aerosol leaving the device during draw. Further discussions relating to the configurations for exterior overwrap materials that may be used with the present disclosure may be found in U.S. Pat. No. 9,078,473 to Worm et al., which is incorporated herein by reference in its entirety.

In various embodiments, other components may exist between the substrate portion 110 and the mouth section 108 of the aerosol source member 104. For example, in some embodiments one or any combination of the following may be positioned between the substrate portion 110 and the mouth section 108 of the aerosol source member 104: an air gap; a hollow tube structure; phase change materials for cooling air; flavor releasing media; ion exchange fibers capable of selective chemical adsorption; aerogel particles as filter medium; and other suitable materials. Some examples of possible phase change materials include, but are not limited to, salts, such as $AgNO_3$, $AlCl_3$, $TaCl_3$, $InCl_3$, $SnCl_2$, $AlI_3$, and $TiI_4$; metals and metal alloys such as selenium, tin, indium, tin-zinc, indium-zinc, or indium-bismuth; and organic compounds such as D-mannitol, succinic acid, p-nitrobenzoic acid, hydroquinone and adipic acid. Other examples are described in U.S. Pat. No. 8,430,106 to Potter et al., which is incorporated herein by reference in its entirety.

As will be discussed in more detail below, the present disclosure is configured for use with a conductive and/or inductive heat source to heat a substrate material to form an aerosol. In some embodiments, a conductive heat source may comprise a heating assembly that comprises a resistive heating source. Resistive heating sources may be configured to produce heat when an electrical current is directed therethrough. Electrically conductive materials useful as resistive heating sources may be those having low mass, low density, and moderate resistivity and that are thermally stable at the temperatures experienced during use. Useful heating sources heat and cool rapidly, and thus provide for the efficient use of energy. Rapid heating of the member may be beneficial to provide almost immediate volatilization of an aerosol precursor material in proximity thereto. Rapid cooling prevents substantial volatilization (and hence waste) of the aerosol precursor material during periods when aerosol formation is not desired. Such heating sources may also permit relatively precise control of the temperature range experienced by the aerosol precursor material, especially when time based current control is employed. Useful electrically conductive materials may be chemically non-reactive with the materials being heated (e.g., aerosol precursor materials and other inhalable substance materials) so as not to adversely affect the flavor or content of the aerosol or vapor that is produced. Some example, non-limiting, materials that may be used as the electrically conductive material include carbon, graphite, carbon/graphite composites, metals, ceramics such as metallic and non-metallic carbides, nitrides, oxides, silicides, inter-metallic compounds, cermets, metal alloys, and metal foils. In particular, refractory materials may be useful. Various, different materials can be mixed to achieve the desired properties of resistivity, mass, and thermal conductivity. In specific embodiments, metals that can be utilized include, for example, nickel, chromium, alloys of nickel and chromium (e.g., nichrome), and steel. Materials that can be useful for providing resistive heating are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

In various embodiments, a heating source may be provided in a variety of forms, such as in the form of a foil, a foam, a mesh, a hollow ball, a half ball, discs, spirals, fibers, wires, films, yarns, strips, ribbons, or cylinders. Such heating sources often comprise a metal material and are configured to produce heat as a result of the electrical resistance associated with passing an electrical current therethrough. Such resistive heating sources may be positioned in proximity to, and/or in direct contact with, the substrate portion 110. For example, in one embodiment, a heating source may comprise a cylinder or other heating device located in the control body 102, wherein the cylinder is constructed of one or more conductive materials, including, but not limited to, copper, aluminum, platinum, gold, silver, iron, steel, brass, bronze, carbon (e.g., graphite), or any combination thereof. In various embodiments, the heating source may also be coated with any of these or other conductive materials. The heating source may be located adjacent an engagement end of the control body 102, and may be configured to substantially surround a portion of the heated section 106 of the aerosol source member 104 that includes the substrate portion 110. In such a manner, the heating source may be located adjacent the substrate portion 110 of the aerosol source member 104 when the aerosol source member is inserted into the control body 102. In other examples, at least a portion of a heating source may penetrate at least a portion of an aerosol source member (such as, for example, one or more prongs and/or spikes that penetrate an aerosol source member), when the aerosol source member is inserted into the control body 102. Although in some embodiments, the heating source may comprise a cylinder, it should be noted that in other embodiments, the heating source may take a variety of forms and, in some embodiments, may make direct contact with and/or penetrate the substrate portion 110.

As described above, in addition to being configured for use with a conductive heat source, the present disclosure may also be configured for use with an inductive heat source to heat a substrate portion to form an aerosol. In various embodiments, an inductive heat source may comprise a resonant transformer, which may comprise a resonant transmitter and a resonant receiver (e.g., a susceptor). In some embodiments, the resonant transmitter and the resonant receiver may be located in the control body 102. In other embodiments, the resonant receiver, or a portion thereof, may be located in the aerosol source member 104. For example, in some embodiments, the control body 102 may include a resonant transmitter, which, for example, may comprise a foil material, a coil, a cylinder, or other structure configured to generate an oscillating magnetic field, and a resonant receiver, which may comprise one or more prongs that extend into the substrate portion 110 or are surrounded by the substrate portion 110.

According to some example embodiments, a change in current in the resonant transmitter, as directed thereto, for example, from a power source by a control component, may produce an alternating electromagnetic field that penetrates the resonant receiver, thereby generating electrical eddy currents within the resonant receiver. The alternating electromagnetic field may be produced by directing alternating current to the resonant transmitter. In some embodiments, the control component may include an inverter or inverter circuit configured to transform direct current provided by the power source to alternating current that is provided to the resonant transmitter.

The eddy currents flowing in the material defining the resonant receiver may heat the resonant receiver through the Joule effect, wherein the amount of heat produced is proportional to the square of the electrical current times the electrical resistance of the material of the resonant receiver. In embodiments of the resonant receiver comprising ferromagnetic materials, heat may also be generated by magnetic hysteresis losses. Several factors contribute to the temperature rise of the resonant receiver including, but not limited to, proximity to the resonant transmitter, distribution of the magnetic field, electrical resistivity of the material of the resonant receiver, saturation flux density, skin effects or depth, hysteresis losses, magnetic susceptibility, magnetic permeability, and dipole moment of the material.

In this regard, in some embodiments both the resonant receiver and the resonant transmitter may comprise an electrically conductive material. By way of example, the resonant transmitter and/or the resonant receiver may comprise various conductive materials including metals such as cooper and aluminum, alloys of conductive materials (e.g., diamagnetic, paramagnetic, or ferromagnetic materials) or other materials such as a ceramic or glass with one or more conductive materials imbedded therein. In another embodiment, the resonant receiver may comprise conductive particles. In some embodiments, the resonant receiver may be coated with or otherwise include a thermally conductive passivation layer (e.g., a thin layer of glass).

In some embodiments, a resonant transmitter may comprise a helical coil configured to circumscribe a cavity into which an aerosol source member, and in particular, a substrate portion of an aerosol source member, is received. In some embodiments, the helical coil may be located between an outer wall of the device and the receiving cavity. In one embodiment, the coil winds may have a circular cross section shape; however, in other embodiments, the coil winds may have a variety of other cross section shapes, including, but not limited to, oval shaped, rectangular shaped, L-shaped, T-shaped, triangular shaped, and combinations thereof. In another embodiment, a pin may extend into a portion of the receiving cavity, wherein the pin may comprise the resonant transmitter, such as by including a coil structure around or within the pin. In various embodiments, an aerosol source member may be received in the receiving cavity wherein one or more components of the aerosol source member may serve as the resonant receiver. Other possible resonant transformer components, including resonant transmitters and resonant receivers, are described in U.S. Patent Application Pub. No. 2019/0124979, titled Induction Heated Aerosol Delivery Device, which is incorporated herein by reference in its entirety.

As noted above, in various embodiments the substrate portion 110 may comprise a cellulose material (such as, for example, a nanocellulose material), at least partially formed from cellulose fibers (e.g., nanocellulose), impregnated with an aerosol precursor composition. As used herein, nanocellulose material refers to cellulose materials having at least one average particle size dimension in the range of 1 nm to 100 nm. Although larger cellulose material sizes could be used, a reduction in aerosol precursor loading would likely result. As a non-limiting example, a suitable nanocellulose material may be a fibrous material prepared from any variety of cellulose-containing materials, such as wood (e.g., eucalyptus trees), grasses (e.g., bamboo), cotton, tobacco, algae, and other plant-based materials, wherein the fiber is further refined such that a nano-fibrillated cellulose fiber is produced. In various embodiments, the nanocellulose material can contain one or more of tobacco-derived nanocellulose fibers and/or non-tobacco-derived nanocellulose fibers, optionally in combination with one or more additional cellulose materials, such as tobacco-derived cellulosic pulp and/or wood pulp-based cellulose fibers. In some embodiments, the substrate portion 110 may further comprise a hydrophobic additive component, a burn retardant material, a flavorant, and conductive fibers or particles for heat conduction/induction, or any combination thereof. Further, in various embodiments, the form of the substrate portion 110 may include gels, shreds, films, suspensions, extrusions, shavings, capsules, and/or particles (including pellets, beads, strips, or any desired particle shape of varying sizes) and combinations thereof. In some embodiments, the substrate portion 110 may not comprise tobacco. In various other embodiments, the substrate portion 110 may not comprise nicotine. In some embodiments, the substrate portion 110 may further comprise one or more of a non-tobacco-derived nicotine and a flavorant. In certain embodiments, the substrate portion 110 may further comprise one or more pharmaceutical agents. In some embodiments, the substrate portion 110 may further comprise one or more non-tobacco botanicals.

The pharmaceutical agent can be any known agent adapted for therapeutic, prophylactic, or diagnostic use. These can include, for example, synthetic organic compounds, proteins and peptides, polysaccharides and other sugars, lipids, inorganic compounds, and nucleic acid sequences, having therapeutic, prophylactic, or diagnostic activity.

In some embodiments, the aerosol precursor composition may incorporate nicotine, which may be present in various concentrations. The source of nicotine may vary, and the nicotine incorporated in the aerosol precursor composition may derive from a single source or a combination of two or more sources. For example, in some embodiments the aerosol precursor composition may include nicotine derived from tobacco. In other embodiments, the aerosol precursor composition may include nicotine derived from other organic plant sources, such as, for example, non-tobacco plant sources including plants in the Solanaceae family. In other embodiments, the aerosol precursor composition may include synthetic nicotine. In some embodiments, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As used herein, the term "botanical material" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, or other treatment processes capable of altering the chemical nature of the material). For the purposes of the present disclosure, a "botanical material" includes but is not limited to "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). The botanical materials used in the present invention may comprise, without limitation, any of the compounds and sources set forth herein, including mixtures thereof. Certain botanical materials of this type are sometimes referred to as dietary supplements, nutraceuticals, "phytochemicals," or "functional foods."

Exemplary botanical materials, many of which are associated with antioxidant characteristics, include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and silybum marianum.

In certain embodiments, the nanocellulose material is admixed with a reconstituted tobacco material, using, for example, various casting and paper-making techniques known in the art. The reconstituted tobacco material can include wood pulp, tobacco fibers, botanicals, or other cellulose components in addition to the nanocellulose material. In some embodiments, the addition of the nanocellulose material to the reconstituted tobacco material can serve to enhance both absorbency and mechanical strength of the resulting material. Reconstituted tobacco materials, and methods of providing such materials, are set forth in U.S. Pat. No. 4,674,519 to Keritsis et al.; U.S. Pat. No. 4,807,809 to Pryor et al.; U.S. Pat. No. 4,889,143 to Pryor et al.; U.S. Pat. No. 4,941,484 to Clapp et al.; U.S. Pat. No. 4,972,854 to Kiernan et al.; U.S. Pat. No. 4,987,906 to Young et al.; U.S. Pat. No. 5,025,814 to Raker; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,707 to Kumar; each of which is incorporated herein by reference in its entirety.

In one particular embodiment, a tobacco-derived nanocellulose material can be formed by receiving a tobacco pulp in a dilute form such that the tobacco pulp is a tobacco pulp suspension with a consistency of less than 5%, and mechanically fibrillating the tobacco pulp suspension to generate a tobacco-derived nanocellulose material. The method for generating tobacco pulp generally comprises heating the tobacco material in a strong base to separate the undesired components such as hemicelluloses and lignin present in the tobacco raw material from cellulose, and filtering the resulting mixture to obtain the desired cellulose material with the least amount of impurities. The resulting tobacco pulp can be further modified to produce numerous nanocellulose materials such as cellulose nanofibrils (CNF), cellulose nanocrystals (CNC), and cellulose microfibrils (CMF), differing from each other mainly based on their isolation methods from the tobacco pulp. The nanocellulose materials described herein will typically comprise materials where particles (whether unbound or as part of an aggregate or agglomerate) within a given particle distribution exhibit at least one average particle size dimension in the range of 1 nm to 100 nm. Average particle sizes can be determined by review of a select number of particle images using transmission electron microscopy (TEM) and averaging the result. Materials and methods that can be useful for providing tobacco-derived nanocellulose are described in U.S. Pat. No. 10,196,778 to Sebastian et al., which is incorporated herein by reference in its entirety. In some embodiments, nanocellulose materials and conventional wood pulp-based cellulose fibers may be used in combination to form substrate materials.

In some embodiments, the nanocellulose material comprises an apparent viscosity ranging from 5,000 to 40,000 mPa*s, from 20,000 to 35,000 mPa*s, or from 20,000 to 30,000 mPa*s at a consistency of 1.5%. Apparent viscosity is measured at 1.5% fixed consistency with Brookfield rheometer RVDV-III at 10 rpm and using the vane spindles.

In some embodiments, the tensile strength of the nanocellulose substrate material is greater than 120 Mpa, or greater than 130 Mpa or greater than 140 Mpa (e.g., ranges from 140 to 180 MPa or from 150 to 170 Mpa). In some embodiments, the strain of the nanocellulose-based substrate material is at least 11% or at least 12%, such as a range from 10% to 15%, or from 11% to 14%. In some embodiments, the tensile modulus of the nanocellulose-based substrate material is at least 4 Gpa, such as a range from 4 to 6 Gpa. Tensile properties can be measured using a modified SCN P 38:80 Paper and board-Determination of tensile strength-procedure; Vartiainen et al. "Hydrophobization of cellophane and cellulose nanofibrils films by supercritical state carbon dioxide impregnation with walnut oil" Biorefinery, vol. 31 no. (4) 2016, which is hereby incorporated by reference in its entirety. Cross-head speed during test is 2 mm/min and the sample width is 15 mm. Gauge length is 20 mm.

In some embodiments, the oxygen permeability of the nanocellulose-based substrate material is less than 0.2, or less than 0.1, or less than 0.05 cc×mm/m$^2$×day at a temperature of 23° C. and at a relative humidity (RH) of 0%, and less than 20, or less than 10, or less than 5 cc×mm/m$^2$×day at a temperature of 23° C. and at a relative humidity (RH) of 80%. Oxygen permeability can be measured using ASTM D3985; Vartiainen et al. "Hydrophobization of cellophane and cellulose nanofibrils films by supercritical state carbon dioxide impregnation with walnut oil" Biorefinery, vol. 31 no. (4) 2016, which is hereby incorporated by reference in its entirety.

In some embodiments, the substrate portion 110 is loaded with an aerosol precursor composition. In various embodiments, loading of the substrate portion 110 is achieved by impregnating the nanocellulose material with the aerosol precursor composition. In some embodiments, the nanocellulose material is impregnated with an aerosol precursor composition at a loading of at least 20%, at least 25%, or at least 30% by weight, at least 35% by weight, at least 40% by weight, at least 45% by weight, or at least 50% by weight, based on a total weight of the impregnated material. Example ranges of aerosol precursor material include 20% to 60% by weight, such as 25% to 50% or 30% to 45%, based on the total weight of the impregnated material. Methods for loading aerosol precursor compositions onto substrate portions are described in U.S. Pat. No. 9,974,334 to Dooly et al., and U.S. Publication Patent Application Nos. 2015/0313283 to Collett et al. and 2018/0279673 to Sebastian et al., the disclosures of which are incorporated by reference herein in their entirety.

Nanocellulose materials are naturally hydrophilic in nature (although such materials can be inherently hydrophobic when using certain manufacturing processes), and thus exhibit a high degree of absorption of hydrophilic aerosol precursor materials such as glycerin. In certain embodiments, the hydrophobicity of the nanocellulose substrate material can be enhanced in order to improve chemical compatibility of the substrate material with a hydrophobic component of an aerosol precursor material, such as menthol. Enhancing hydrophobicity of a nanocellulose material surface typically involves either physical interaction/adsorption of hydrophobic molecules onto the surface or grafting hydrophobic molecules onto the surface via chemical bonding, or a combination of such techniques. Examples of agents that can be physically adsorbed or otherwise associated with a nanocellulose surface include poly-DADMAC (polydiallyldimethylammonium chloride), cetrimonium bromide, and perfluoro-octadecanoic acid. Examples of chemical modification/grafting agents include acetic anhydride, hexamethyldisilazane, and hydroxyethylmethacrylate. Methylation and silylation are examples of grafting techniques that can increase hydrophobicity of a surface. See also, the additives set forth in Missoum et al. Nanofibrillated Cellulose surface Modifications: A Review, Materials, 2013, 6, 1745-1766; Dufresne et al, Nanocellulose: a new ageless bio nanomaterial, Materials Today, 16 (6), 2013, 220-227; Peng et al, Chemistry and applications of nanocrystalline cellulose and its derivatives: A nanotechnology perspective, Canadian Journal of Chemical Engineering, 9999, 2011, 1-16; and Wang and Piao, From hydrophilicity to hydrophobicity: a critical review—part II: hydrophobic conversion, Wood and Fiber Science, 43(1), 2011, 41-46.

As noted, in various embodiments, the substrate portion 110 may include an additive component that increases the hydrophobicity of the substrate. In various embodiments, the additive component in the substrate portion 110 is added to the nanocellulose material prior to impregnating the nanocellulose material, such that the additive component chemically or physically modifies the nanocellulose material making it more hydrophobic, further allowing the nanocellulose material to undergo increased loading of hydrophobic aerosol precursor materials, such as menthol. Examples of suitable hydrophobic aerosol precursor compositions for loading onto nanocellulose materials include flavorants selected from the group consisting of esters, terpenes (including cyclic terpenes), aromatics, and lactones. Additional examples of suitable hydrophobic aerosol precursor compositions include, but are not limited to, methyl butyrate, ethyl butyrate, isoamyl acetate, pentyl pentanoate, citral, nerol, limonene, citronella, menthol, carvone, eugenol, anisole, benzaldehyde, massoia lactone, sotolone, jasmine lactone, gamma-decalactone, geraniol, and delta-decalactone. The hydrophobic component can also be an essential oil (e.g., peppermint oil, orange oil, and the like) or other plant extracts, absolutes or oleoresins (e.g., fenugreek, ginger, and the like).

In certain other embodiments, the substrate portion 110 may be divided into various sub-portions. In some embodiments, one or more of the sub-portions may include an additive component that increases the hydrophobicity of that sub-portion (hereinafter, "treated sub-portion") and one or more of the sub-portions may not include a hydrophobic additive component (hereinafter, "untreated sub-portion"). Advantageously, this allows for one or more untreated sub-portions that comprise hydrophilic nanocellulose materials and one or more treated sub-portions that comprise hydrophobic nanocellulose materials. In some embodiments, the untreated sub-portions may be positioned closer to the heat source as compared to the treated sub-portions to facilitate more heat to the untreated sub-portions. In certain other embodiments, the substrate portion 110 may comprise a segmented configuration of treated and untreated sub-portions, such that the sub-portions are intimately arranged in an end to end configuration. Such configurations allow for a gradient substrate wherein the hydrophobicity of each sub-portion increases the farther in proximity the sub-portion is from the heat source. Generally, sub-portions with higher hydrophobicity concentrations, require lower amounts of heat in order to release the aerosol precursor compositions within the sub-portions. In various embodiments, treated sub-portions and untreated sub-portions may be shredded and dispersed among each other such that the substrate portion 110 comprises a co-mingling of treated sub-portions and untreated sub-portions in a shredded form.

As noted, the substrate portion 110 may also include a burn retardant material. One example of such a material is ammonium phosphate. In some embodiments, other flame/burn retardant materials and additives may be included within the substrate portion 110 and may include organo-phosphorus compounds, borax, hydrated alumina, graphite, potassium, silica, tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides may also be used. In each aspect of flame-retardant, burn-retardant, and/or scorch-retardant materials used in the substrate material and/or other components (whether alone or in combination with each other and/or other materials), the desirable properties are independent of and resistant to undesirable off-gassing or melting-type behavior. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Patent Application Publication No. 2007/0215167 to Crooks et al.; the disclosures of which are incorporated herein by reference in their entireties.

As noted, the substrate portion 110 may be impregnated with an aerosol precursor composition. In some embodiments, the aerosol precursor composition may comprise glycerin, propylene glycol, or medium chain triglycerides. Aerosol forming materials include polyhydric alcohols (e.g., glycerin, propylene glycol, and triethylene glycol) and/or water, and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Patent Application Publication No. WO 98/57556 to Biggs et al.; and Chemical and Biological Studies on New Cigarette Prototypes that Heat Instead of Burn Tobacco, R. J. Reynolds Tobacco Company Monograph (1988); which are incorporated herein by reference in their entirety. Other representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Patent Pub. Nos. 2013/0008457 to Zheng et al.; 2015/0020823 to Lipowicz et al.; 2015/0020830 to Koller; and 2017/0367386 to McElvany et al., as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B. V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Embodiments of effervescent materials can be used with the aerosol precursor composition, and are described, by way of example, in U.S. Patent Application Publication No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Patent Application Publication No. 2010/0018539 to Brinkley et al. and PCT Application Publication No. WO 97/06786 to Johnson et al., all of which are incorporated by reference herein in their entireties. Additional description with respect to embodiments of aerosol precursor compositions, including description of tobacco or components derived from tobacco included therein, is provided in U.S. Patent Application Publication Nos. 2018/0020722 and 2018/0020723, each to Davis et al., which are incorporated herein by reference in their entireties.

As noted, the substrate portion 110 may also include a flavorant. As used herein, reference to a "flavorant" refers to compounds or components that can be aerosolized and delivered to a user and which impart a sensory experience in terms of taste and/or aroma. Some examples of flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Some examples of plant-derived compositions that may be suitable are disclosed in U.S. Pat. No. 9,107,453 and U.S. Patent Application Publication No. 2012/0152265 both to Dube et al., the disclosures of which are incorporated herein by reference in their entireties. The selection of such further components is variable based upon factors such as the sensory characteristics that are desired for the smoking article, their affinity for the substrate material, their solubilities, and other physiochemical properties. The present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As noted, the substrate portion 110 may also include conductive fibers or particles for heat conduction or heating by induction. In some embodiments, the conductive fibers or particles may be arranged in a substantially linear and parallel pattern. In some embodiments, the conductive fibers or particles may have a substantially random arrangement. In some embodiments, the conductive fibers or particles may be constructed of or more of an aluminum material, a stainless steel material, a copper material, a carbon material, and a graphite material. In some embodiments, one or more conductive fibers or particles with different Curie temperatures may be included in the substrate material to facilitate heating by induction at varying temperatures.

Referring to FIG. 3, in the depicted embodiment the substrate portion 110 of the inserted source member 104 is segmented into multiple substrate segments that are associated with multiple heating segments of the heat source of the control body 102. In the depicted embodiment, the heat source of the control body 102 includes a first heating segment 132, a second heating segment 134, and a third heating segment 136. As shown, the substrate portion 110 includes a first substrate segment 142 associated with the first heating segment 132, a second substrate segment 144 associated with the second heating segment 134, and a third substrate segment 146 associated with a third heating segment 136. In some embodiments, the heat source may include less than or more than three heating segments and the heated section 106 may include less than or more than three respective substrate segments. In some embodiments, the heat source may include more or less heating segments than respective substrate segments of the heated section 106. In some embodiments, the aerosol source member 104 may include an aerosol pathway 116 that passes through the substrate segments 142, 144, 146. The aerosol pathway 116 may be disposed about a central longitudinal axis of the aerosol source member 104. In the depicted embodiment, the heating segments 132, 134, 136 of the heat source are arranged, from distal to downstream of the control body 102, with the first heating segment 132 distal to the second heating segment 134 and the second heating segment 134 distal to the third heating segment 136. In this configuration, the second heating segment 134 is positioned between the first and third heating segments 132, 136. Similarly, the substrate segments 142, 144, 146 are arranged with the second substrate segment 144 downstream from the first substrate segment 142 and the third substrate segment 146 downstream from the second substrate segment 146. In this configuration, the second substrate segment 144 is positioned between the first and third substrate segments 142, 146. In the depicted embodiment, the downstream end of the aerosol source member 104 comprises a mouth-end of the aerosol source member 104, which includes a filter 114. It should be noted, however, that in other implementations, the downstream end of an aerosol source member may not comprise a mouth-end and/or may not include a filter.

Although in the depicted embodiments the heat source has multiple heating segments (e.g., two or more heating segments), in other embodiments the heat source may have one heating segment that heats multiple substrate segments (e.g., two or more substrate segments) to different temperatures. For example, a heat source having one heating segment may create a temperature gradient across multiple substrate segments (e.g., based on proximity or distance from the heat source) such that multiple substrate segments are heated to different temperatures. It should further be noted that although the depicted embodiment shows an aerosol source member that extends outside of a control body, it should be noted that the present invention should not be so limited. In other embodiments, for example, an aerosol source member may be fully received and/or concealed within a control body. In particular, in some embodiments a source member may be fully received into a receiving compartment or chamber of a control body. In addition, in some embodiments there may be a mouthpiece, while other embodiments need not include a mouthpiece. In some embodiments, the mouthpiece may be a separate component (and, in some embodiments, may be reusable). In addition, in some embodiments the source member may comprise a substrate portion and need not include a filter or other segments or sections.

Referring back to FIG. 3, when the heating segments 132, 134, 136 of the depicted embodiment are activated, the first heating segment 132 is configured to heat the first substrate segment 142 to a first temperature, the second heating segment 134 is configured to heat the second substrate segment 144 to a second temperature less than the first temperature, and the third heating segment 136 is configured to heat the third substrate segment 146 to a third temperature less than the second temperature. In this configuration, the temperature within the heated section 106 decreases from a distal end to a downstream end thereof. The first heating segment 132 may terminate before a downstream end of the first substrate segment 142 and a distal end of the second substrate segment 144 such that the first temperature is limited to the first substrate segment 142 and the second substrate segment 144 is prevented from exceeding a desired temperature (e.g., the second temperature). Similarly, the second heating segment 134 may terminate before a downstream end of the second substrate segment 142 and a distal end of the third substrate segment 146 such that the third substrate segment 146 is prevented from exceeding the third temperature. The heating segments 132, 134, 136 may be inductive or conductive heating sources. In some embodiments, the heating segments 132, 134, 136 are positioned along the substrate segments 142, 144, 146. Additionally or alternatively, the heating segments 132, 134, 136 are positioned within the substrate segments 142, 144, 146.

The first temperature may be in a range of 240° C. to 350° C. (e.g., 300° C.), the second temperature may be in a range of 180° C. to 250° C. (e.g., 200° C.), and the third temperature may be in a range of 80° C. to 225° C. (e.g., 100° C.). In some embodiments, the first, second, and third temperatures may be configured to enable vapor formation of an aerosol former disposed within each of the substrate segments 142, 144, 146 while reducing or avoiding formation of unwanted byproducts, such as off flavors that may result from overheating a substrate and/or production of harmful and potentially harmful constituents (HPHCs) as defined by the United States Food and Drug Administration that may result from overheating some substrate materials and/or aerosol formers. The first substrate segment 142 may include a first aerosol former 152 having a high boiling point and/or a low volatility index. The first aerosol former 152 may include nicotine and, in some embodiments, flavor elements that require high temperatures to form vapors. The first aerosol former 152 may be in the form of beads packed within the first substrate segment 142 and/or may be suspended in a cellulose, fibrous, non-fibrous, or inert substrate that is resistant to heat. The first temperature may be determined to heat the first aerosol former 152 without burning the first aerosol former 152 and/or a substrate that the first aerosol former 152 is suspended therein. The first temperature may be determined to enable a flavor profile of an aerosol formed from the first aerosol former 152. The first aerosol former 152 may be suspended in glycerol to form a vapor as the glycerol is heated to the first temperature. The first aerosol former 152 may include, but is not limited to, maltol, vanillin, ethyl vanillin, cinnamic acid, phenylacetic acid, levulinic acid, nerolidol, citronellyl phenylacetate, caryophyline oxide, gamma nonalactone, isoamyl phenylacetate, phenylethyl isovalerate, heliotropin, or combinations thereof.

The second substrate segment 144 may include a second aerosol former 154 having a lower boiling point and/or a higher volatility index than the first aerosol former 152. The second aerosol former 154 may include flavor elements that are configured to enhance an aerosol that is drawn downstream through the aerosol source member 104. In embodiments, the second aerosol former 154 may include tobacco. The second aerosol former 154 may be in the form of beads packed within the second substrate segment 144 and/or may be suspended in a cellulose, fibrous, non-fibrous, or inert substrate that is resistant to heat in a manner similar to the first aerosol former 152. The second temperature may be determined to heat the second aerosol former 154 without burning the second aerosol former 154 and/or a substrate that the second aerosol former 154 is suspended therein. The second temperature may be determined to enable a flavor profile of an aerosol formed from the second aerosol former 154. The second aerosol former 154 may be suspended in propylene glycol. The second aerosol former may also include glycerol or be suspended within glycerol to enhance flavor mixing. The second aerosol former 154 may include, but is not limited to, 2-acetylpyrrole, methyl cyclopentenolone, alpha-ionone, geraniol, beta-damascene, menthol, caryophyllene, caproic acid, phenethyl alcohol, anethole, phenethyl butyrate, alpha terpineol, ethyl phenylacetate, 3-methylvaleric acid, propylene glycol, benzyl alcohol, or combinations thereof.

The third substrate segment 146 may include a third aerosol former 156 having a lower boiling point and/or a higher volatility index than the first and second aerosol formers 152, 154. The third aerosol former 156 may include flavor elements and/or tobacco that is configured to enhance an aerosol that is drawn downstream through the aerosol source member 104. The third aerosol former 156 may be in the form of beads packed within the third substrate segment 146 and/or may be suspended in a cellulose, fibrous, non-fibrous, or inert substrate that is resistant to heat in a manner similar to the first aerosol former 154. In embodiments, the third aerosol former 156 includes tobacco formed into a rod and/or packed within the third substrate segment 146. The third temperature may be determined to heat the third aerosol former 156 without burning the third aerosol former 156 and/or a substrate that the third aerosol former 156 is suspended therein. The third temperature may be determined to enable a flavor profile of an aerosol formed from the third aerosol former 156. The third aerosol former 156 may include, but is not limited to, 3-acetylpyridine, tetramethylpyrazine, methyl salicylate, linalool, ethyl caproate, gamma-valerolactone, para-tolylaldehyde, 2-methylbutyric acid, isovaleric acid, benzaldehyde, limonene, 2-methylpyrazine, or combinations thereof.

As noted, in some embodiments the third aerosol former 156 may include tobacco. The third substrate segment 146 may have a maximum temperature below a temperature at which tobacco in the third aerosol former 156 degrades (e.g., 100° C.). In some embodiments, the second substrate segment 144 may have a maximum temperature below a temperature at which tobacco in the second substrate segment degrades (e.g., 150° C.). Specifically, oriental and/or flue cured tobacco may be included in the second aerosol former 154 and burley tobacco may be more suited for inclusion in the third aerosol former 156.

In embodiments, nicotine salts may be included in one or more of the aerosol formers 152, 154, 156. The boiling point and/or the volatility of a nicotine salt may depend on a vapor pressure of an acid used to form the salt such that a particular nicotine salt may be more suitable for a particular one of the substrate segments 142, 144, 146. For example, a nicotine lactate, nicotine levulinate, or nicotine benzoate may be suitable in the first aerosol former 152 within the first substrate segment 142 and nicotine L-malate or nicotine mucate may be suitable in the second aerosol former 154 within the second substrate segment 144.

Segmenting the heated section 106 of the aerosol source member 104 of some embodiments allows for vapor formation from each of the aerosol formers 152, 154, 156 to be generated while reducing potential creation of unwanted byproducts during vapor formation. In addition, segmenting the heated section 106 may allow for more complete vapor formation of each of the aerosol formers 152, 154, 156 when compared to a non-segmented heated section 106. Further, segmenting the heated section 106 may allow for combinations of high boiling point and/or low volatility aerosol formers with low boiling point and/or high volatility aerosol formers in a single source member 104. Segmenting the heated section 106 may also improve flavor profiles of an aerosol when compared to an unsegmented heated section.

The first, second, or third aerosol formers 152, 154, 156 may include a series of overlapping layers of a composite substrate sheet that has a nanocellulose material. A layer of the nanocellulose material may be formed by any suitable method, such as wet-laid methods and dry-laid methods (e.g., carding or air-laid methods). The resulting layer of nanocellulose fibers can be in the form of a film or a sheet. If desired, an additive component may be used, such as additive components that typically allow cellulose-based fiber sheets to undergo a chemical modification to increase hydrophobicity. In various embodiments, the nanocellulose film or sheet may be impregnated with an aerosol precursor composition and/or additional flavorants to form the first, second, or third aerosol formers 152, 154, 156. The nanocellulose sheet or film may be formed without the use of a polymeric binder as is typically required when forming cohesive sheet materials. In particular embodiments, nanocellulose materials, alone, can act as the binder in a nanocellulose sheet or film. Accordingly, in certain embodiments, a sheet material comprising the nanocellulose material is formed using a casting or paper-making process and the sheet material incorporates one or more aerosol-forming materials and, optionally, one or more flavorants. However, the sheet material can be substantially free or completely free of polymeric binder (e.g., less than 1% by weight or less than 0.5% by weight or less than 0.1% by weight polymeric binder based on total weight of the sheet). In other embodiments, the sheet material can include a polymeric binder to supplement the binding properties of the nanocellulose material. For additional details of suitable naoncellulose materials reference can be made to U.S. patent application Ser. No. 16/294,098, filed Mar. 6, 2019, the entire contents of which are hereby incorporated by reference.

Although in some embodiments an aerosol source member 104 and a control body 102 may be provided together as a complete smoking article or pharmaceutical delivery article generally, the components may be provided separately. For example, the present disclosure also encompasses a disposable unit for use with a reusable smoking article or a reusable pharmaceutical delivery article. In specific embodiments, such a disposable unit (which may be an aerosol source member as illustrated in the appended figures) can comprise a substantially tubular shaped body having a heated end configured to engage the reusable smoking article or pharmaceutical delivery article, an opposing mouth section configured to allow passage of an inhalable substance to a consumer, and a wall with an outer surface and an inner surface that defines an interior space. Various embodiments of an aerosol source member (or cartridge) are described in U.S. Pat. No. 9,078,473 to Worm et al., which is incorporated herein by reference in its entirety.

Although some figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

Referring now to FIG. 4, another aerosol source member 204 is provided in accordance with the present disclosure. Although, as noted above, in other embodiments the heat source may be a non-carbon heat source, in the depicted embodiment the aerosol source member 204 is a carbon heated tobacco product and includes, from a distal end to a downstream end, a carbon heat source 232, a segmented heated section 206, and a filter 214. The aerosol source member 204 may be used with or without a holder. The heated section 206 is similar to the heated section 106 detailed above with like elements including similar labels with the leading "1" replaced with a leading "2". As such, like elements will not be detailed herein for brevity.

In use, the carbon heat source 232 is ignited to burn and generate heat. The heated section 206 is heated by the heat generated by the carbon heat source 232 to form an aerosol from aerosol formers disposed within the heated section 206. As described herein, the heat source 232 is a carbon heat source; however, other heat sources may be used which are capable of providing heat to the heated section 206 in a similar manner to the heat source 232.

With additional reference to FIG. 5, the heated section 206 of some example embodiments may be separated from the heat source 232 by a first barrier 262 positioned between a first substrate segment 242 and the heat source 232. The first barrier 262 is configured to provide a thermal barrier between the heat source 232 and the first substrate segment 242 to maintain a temperature within the first substrate segment 242 at or below a predetermined first maximum temperature (e.g., 300° C.). For example, the heat source 232 may burn at 700° C. and the first barrier 262 may provide a thermal barrier between the heat source 232 and the first substrate segment 242 such that the first substrate segment 242 is at or below 300° C. The first barrier 262 may be fire or burn resistant to prevent ignition of the first barrier 262 and thus, the substrate segment 206.

The heated section 206 may include a second barrier 264 positioned between the first substrate segment 242 and the second substrate segment 244. The second barrier 264 is configured to provide a thermal barrier between the first substrate segment 242 and the second substrate segment 244 to maintain a temperature within the second substrate segment 244 at or below a predetermined second maximum temperature (e.g., 200° C.).

The heated section 206 may include a third barrier 266 positioned between the second substrate segment 244 and a third substrate segment 246. The third barrier 266 is configured to provide a thermal barrier between the second substrate segment 244 and the third substrate segment 246 to maintain a temperature within the third substrate segment 246 at or below a predetermined third maximum temperature (e.g., 100° C.).

One or more of barriers 262, 264, 266 may be embodied as metallic disc (e.g., an aluminum disc) and may include one or more openings to allow air to pass therethrough. In some embodiments, the barriers 262, 264, 266 are formed of metals, silica fibers, silica aerogels, pyrogel, ceramic insulators, cellulose fibers containing silica, refractory fibers, carbon fibers and foams, various phase change materials, or combinations thereof. For example, during use, a user may create a draw through the filter 214 such that air is drawn downstream from the heat source or adjacent the heat source through the first, second, and third substrate segments 242, 244, 246 to draw air through the first, second, and third aerosol formers 252, 254, 256 disposed within a respective one of the first, second, and third substrate segments 242, 244, 246 to draw an aerosol including a desired flavor and/or desired amount of nicotine through the filter 214. The barriers 262, 264, 266 prevent the temperature within each of the substrate segments 242, 244, 246 from exceeding a predetermined temperature as the drawn air passing through such that the first, second, and third aerosol formers 252, 254, 256 form a vapor within a desired temperature range to produce a desired aerosol having a desired flavor and other properties. In addition, preventing the temperature within each of the substrate segments 242, 244, 246 from exceeding a predetermined temperature prevents the respective aerosol formers 252, 254, 256 from degrading or breaking down. It will be appreciated, however, that in some embodiments one or more of the barriers 262, 264, and 266 may be omitted.

Continuing to refer to FIG. 4, the aerosol source member 204 may include an outer wrap 212 to engage or otherwise join together at least a portion of the heat source 232 with the substrate portion 206 and at least a portion of the filter 214. In various embodiments, the outer wrap 212 is configured to be retained in a wrapped position in any manner of ways including via an adhesive, a fastener, or the like to allow the outer wrap 212 to remain in the wrapped position. Otherwise, in some other aspects, the outer wrap 212 may be configured to be removable as desired. For example, upon retaining the outer wrap 212 in a wrapped position, the outer wrap 212 may be able to be removed from the heat source 232, the substrate portion 206, and/or the filter 214.

In some embodiments, in addition to the outer wrap 212, the aerosol delivery device may also include a liner that is configured to circumscribe the substrate portion 206 and at least a portion of the heat source 232. The liner may circumscribe only a portion of the length of the substrate portion 206, in some embodiments, the liner may circumscribe substantially the full length of the substrate portion 206. As such, in some embodiments the outer wrap 212 and the liner may be separate materials that are provided together (e.g., bonded, fused, or otherwise joined together as a laminate). In other embodiments, the outer wrap 212 and the liner may be the same material. In any event, the liner may be configured to thermally regulate conduction of the heat generated by the ignited heat source 232, radially outward of the liner. As such, in some embodiments, the liner may be constructed of a metal foil material, an alloy material, a ceramic material, or other thermally conductive amorphous carbon-based material, and/or an aluminum material, and in some embodiments may comprise a laminate. In some embodiments, depending on the material of the outer wrap 212 and/or the liner, a thin layer of insulation may be provided radially outward of the liner. Thus, the liner may advantageously provide, in some aspects, a manner of engaging two or more separate components of the aerosol source member 204 (such as, for example, the heat source 232, the substrate portion 206, and/or a portion of the filter 214), while also providing a manner of facilitating heat transfer axially therealong, but restricting radially outward heat conduction.

In various embodiments, ignition of the heat source 232 results in aerosolization of the aerosol precursor composition associated with the substrate portion 206. The elements of the substrate portion 206 may not experience thermal decomposition (e.g., charring, scorching, or burning) to any significant degree, and the aerosolized components are entrained in the air that is drawn through the aerosol source member 204, including the filter 214, and into the mouth of the user. In various embodiments, the filter 214 is configured to receive the generated aerosol therethrough in response to a draw applied to the filter 214 by a user. In some embodiments, the filter 214 may be fixedly engaged to the substrate portion 206. For example, an adhesive, a bond, a weld, and the like may be suitable for fixedly engaging the filter 214 to the substrate portion 206. In one example, the filter 214 is ultrasonically welded and sealed to an end of the substrate portion 206. In some embodiments, the aerosol source member 204 may include an intermediate portion disposed between the filter 214 and the substrate portion 206. The intermediate portion may allow for aerosol to gather and/or may reinforce the filter 214 and/or the substrate portion 206.

Tobacco materials that may be useful in the present disclosure can vary and may include, for example, flue-cured tobacco, burley tobacco, Oriental tobacco or Maryland tobacco, dark tobacco, dark-fired tobacco and *Rustica* tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), which may be in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Patent Application Publication No. 2004-0255965 to Perfetti et al.; PCT Patent Application Publication No. WO 02/37990 to Bereman; and Bombick et al., Fund. Appl. Toxicol., 39, p. 11-17 (1997); which are incorporated herein by reference in their entireties. Further examples of tobacco compositions that may be useful are disclosed in U.S. Pat. No. 7,726,320 to Robinson et al., which is incorporated herein by reference in its entirety. In some embodiments, the milled tobacco material may comprise a blend of flavorful and aromatic tobaccos. In another embodiment, the tobacco material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety.

In various embodiments, the heat source 232 may be configured to generate heat upon ignition thereof. In the depicted embodiment, the heat source 232 comprises a combustible fuel element that has a generally cylindrical shape and that incorporates a combustible carbonaceous material. In other embodiments, the heat source 232 may have a different shape, for example, a prism shape having a triangular, cubic, or hexagonal cross-section. Carbonaceous materials generally have a high carbon content. Carbonaceous materials may be composed predominately of carbon, and/or typically may have carbon contents of greater than 60 percent, generally greater than 70 percent, often greater than 80 percent, and frequently greater than 90 percent, on a dry weight basis.

In some instances, the heat source 232 may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite fibers; iron oxide powder; glass filaments; powdered calcium carbonate; alumina granules; ammonia sources, such as ammonia salts; and/or binding agents, such as guar gum, ammonium alginate and sodium alginate). Although specific dimensions of an applicable heat source may vary, in some embodiments, the heat source 232 may have a length in an inclusive range of approximately 7 mm to approximately 20 mm, and in some embodiments may be approximately 17 mm, and an overall diameter in an inclusive range of approximately 3 mm to approximately 8 mm, and in some embodiments may be approximately 4.8 mm (and in some embodiments, approximately 7 mm). Although in other embodiments, the heat source may be constructed in a variety of ways, in the depicted embodiment, the heat source 232 is extruded or compounded using a ground or powdered carbonaceous material, and has a density that is greater than 0.5 $g/cm^3$, often greater than 0.7 $g/cm^3$, and frequently greater than 1 $g/cm^3$, on a dry weight basis. See, for example, the types of fuel source components, formulations and designs set forth in U.S. Pat. No. 5,551,451 to Riggs et al. and U.S. Pat. No. 7,836,897 to Borschke et al., which are incorporated herein by reference in their entireties. Although in various embodiments, the heat source may have a variety of forms, including, for example, a substantially solid cylindrical shape or a hollow cylindrical (e.g., tube) shape, the heat source 232 of the depicted embodiment comprises an extruded monolithic carbonaceous material that has a generally cylindrical shape but with a plurality of grooves (not shown) extending longitudinally from a second end of the extruded monolithic carbonaceous material to an opposing second end of the extruded monolithic carbonaceous material. In some embodiments, the aerosol delivery device, and in particular, the heat source may include a heat transfer component. In various embodiments, a heat transfer component may be proximate the heat source, and, in some embodiments, a heat transfer component may be located in or within the heat source. Some examples of heat transfer components are described in in U.S. patent application Ser. No. 15/923,735, filed on Mar. 16, 2018, and titled Smoking Article with Heat Transfer Component, which is incorporated herein by reference in its entirety.

Generally, the heat source is positioned sufficiently near an aerosol delivery component (e.g., a substrate portion) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device elements are appreciated upon consideration of commercially available electronic aerosol delivery devices, such as those representative products listed in the background art section of the present disclosure.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further embodiments, a kit may comprise a plurality of aerosol source members. A kit may further comprise a plurality of aerosol source members and one or more batteries and/or one or more charging components. In the above embodiments, the aerosol source members or the control bodies may be provided with a heating source inclusive thereto. A kit may further comprise one or more holders and one or more aerosol source members that have ignitable heat sources. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

a control body configured to receive at least a portion of an aerosol source member; and a heat source configured to heat to plurality of heat temperatures, wherein the aerosol source member comprises a segmented substrate portion comprising a first substrate segment including a first aerosol former, and a second substrate segment including a second aerosol former different from the first aerosol former, the second substrate segment positioned between the first substrate segment and a downstream end of the aerosol source member, and wherein the first substrate segment has a first heat temperature and the second substrate has a second heat temperature that is less than the first heat temperature, and further comprising a third substrate segment including a third aerosol former, the third substrate segment positioned between the second substrate segment and a downstream end of the aerosol source member, wherein the third aerosol former is different than the first and second aerosol formers, and wherein the third substrate segment has a third heat temperature that is less than the second temperature, wherein the first, second, and third substrate segments comprise respective first, second, and third volatility indexes, and wherein the volatility index of the first substrate segment is lower than the volatility index of the second substrate segment, and the volatility index of the second substrate segment is lower than the volatility index of the third substrate segment.

2. The aerosol delivery device of claim 1, wherein the heat source comprises a first heating segment and a second heating segment, wherein the first heating segment is configured to heat the first substrate segment to the first heat temperature, and the second heating segment is configured to heat the second substrate segment to the second heat temperature, and further comprising a third heating segment that is configured to heat the third substrate segment to the third heat temperature.

3. The aerosol delivery device of claim 2, wherein the control body includes a power source configured to provide energy to the first and second and third heating segments.

4. The aerosol delivery device according to claim 2, wherein the first heating segment is disposed along at least a portion of the first substrate segment and the second heating segment is disposed along at least a portion of the second substrate segment and the third heating element is disposed along at least a portion of the third substrate segment.

5. The aerosol delivery device according to claim 2, wherein the first heating segment is disposed about the first substrate segment and the second heating segment is disposed about the second substrate segment and the third heating element is disposed about the third substrate segment.

6. The aerosol delivery device according to claim 2, wherein the first and second and third heating segments are electrically powered heating elements.

7. The aerosol delivery device according to claim 2, wherein at least one of the first or second or third heating segments comprises a resistive heating element.

8. The aerosol delivery device according to claim 2, wherein at least one of the first or second or third heating segments comprises an inductive heating element.

9. The delivery device according to claim 1, wherein the control body includes a controller configured to control energy transmitted to the first and second and third heating segments.

10. The aerosol delivery device according to claim 1, wherein the substrate portion defines an aerosol pathway extending towards the downstream end of the aerosol source member.

11. The aerosol delivery device according to claim 1, wherein the heat source comprises a first heating segment, and wherein the first heating segment is configured to heat the first substrate segment to the first heat temperature and is configured to heat the second substrate segment to the second heat temperature and is configured to heat the third substrate segment to the third heat temperature.

12. The aerosol delivery device according to claim 1, wherein the second and third substrate segments comprise flavorants.

13. The aerosol delivery device according to claim 1, wherein the second substrate segment comprises only a flavorant, and wherein the third substrate segment comprises a tobacco material and a flavorant.

14. The aerosol delivery device according to claim 1, wherein the first and second substrate segments comprise non-tobacco materials, and wherein the third substrate segment comprises a tobacco material.

15. The aerosol delivery device of claim 1 further comprising a first barrier positioned between the first substrate segment and the second substrate segment, the first barrier being configured to provide a thermal barrier between the first and second substrate segments, and a second barrier positioned between the second substrate segment and the third substrate segment, the second barrier being configured to provide a thermal barrier between the second and third substrate segments.

16. The aerosol delivery device of claim 15, further comprising a third barrier positioned between the heat source and the first substrate segment, the first barrier being configured to provide a thermal barrier between the heat source and the first substrate segments.

* * * * *